United States Patent
Lytinas

(10) Patent No.: US 6,491,693 B1
(45) Date of Patent: Dec. 10, 2002

(54) METHOD OF PROMOTING OSTEOGENESIS BY APPLICATION OF A VACUUM TO AFFECTED BONE AREAS, AND DEVICE FOR SAME

(76) Inventor: Michael Lytinas, 62 Boylston St., Apt. 109, Boston, MA (US) 02116

( * ) Notice: Subject to any disclaimer, the term of this patent is extended or adjusted under 35 U.S.C. 154(b) by 0 days.

(21) Appl. No.: 09/708,210

(22) Filed: Nov. 8, 2000

Related U.S. Application Data

(60) Provisional application No. 60/169,388, filed on Dec. 7, 1999.

(51) Int. Cl.$^7$ ................................................ A61B 17/56
(52) U.S. Cl. ......................................... 606/53; 606/123
(58) Field of Search ............................ 606/53, 79, 123; 604/115, 902; 433/91, 93

(56) References Cited

U.S. PATENT DOCUMENTS

| | | | |
|---|---|---|---|
| 4,822,278 A | * | 4/1989 | Oliva et al. |
| 5,019,086 A | * | 5/1991 | Neward |
| 5,224,947 A | * | 7/1993 | Cooper et al. |
| 5,810,840 A | * | 9/1998 | Lindsay |
| 5,935,136 A | * | 8/1999 | Hulse et al. |
| 5,964,733 A | * | 10/1999 | Laabs et al. |
| 6,086,587 A | * | 7/2000 | Hawk |

* cited by examiner

Primary Examiner—Pedro Philogene
(74) Attorney, Agent, or Firm—Melvin Blecher

(57) ABSTRACT

A method of stimulating bone regeneration in a local area of a bone in a subject requiring same, comprising the step of applying to said local area of said bone an effective vacuum for an effective length of time.

2 Claims, 7 Drawing Sheets

METHOD OF PROMOTING OSTEOGENESIS BY APPLICATION OF A VACUUM TO AFFECTED BONE AREAS, AND DEVICE FOR SAME

This is a regular application derived from provisional application No. 60/169,388, filed Dec. 7, 1999.

FIELD OF THE INVENTION

The invention is concerned with local bone regeneration. More specifically, the invention relates to the use of locally-applied vacuum to stimulate osteoblastic activity in the area treated.

BACKGROUND OF THE INVENTION

Osteogenesis, the growth of new bone, is a part of the normal healing process, and involves recruiting and activating osteoblast cells in bone. This can be a slow process, particularly in the elderly and after severe trauma to the bone and after disease. The ability to accelerate osteogenesis would speed the healing process after trauma and after orthopedic and dental procedures. Methods to accelerate the process, particularly in local areas of bone, have been a holy grail for scientists for many years. The holy grail has not yet been found.

Current techniques of bone regeneration include: traditional methods such as distraction osteogenesis in which bone is pulled in an appropriate direction to stimulate growth, and bone grafting; and, experimental techniques that include use of drugs such as OP-1 that stimulate osteoblasts, implanting biomaterials laced with molecular signals designed to trigger the body's own repair mechanism, injecting bone marrow stem cells into the affected areas, and, transfusing cells that carry genes that code for bone-repair proteins. None of these methods are yet totally satisfactory, for a host of reasons. For a review of this subject see: Service, *Science*, 289:1498 (2000).

Distraction osteogenesis requires a bulky device and requires a very long period before positive results are seen. Bone grafting is limited by the quantity and quality of the patient's bone available for grafting. Biocompatible polymeric matrices without or with natural or recombinant bone morphogenic proteins suffer from a need for very large and very expensive quantities of these signal proteins. The gene therapy procedure suffers from the general problems of gene therapy in general. The use of the stem cell approach is greatly limited by the scarcity and expense of such cells; for example, in 50-year olds, there is only one stem cell in 400,000 bone marrow cells (see Service, 2000, above.

Clearly, there is an acute need for a safe, simple, rapid, inexpensive and efficient method for producing osteogenesis in selected areas of bone. Such a method has been discovered, and is described below.

SUMMARY OF THE INVENTION

A method of producing bone regeneration (osteogenesis) in a local area of a bone in a subject requiring same, comprising the step of applying to the local area of the bone a vacuum (subatmospheric pressure) for an effective length of time.

In one embodiment, the local area of the bone is sealed from the atmosphere with a flexible, sterilizable suction cup device of a dimension and curvature suitable to enclose and fit tightly over the desired local area of the bone. The cup is then evacuated by means of an entry port in the base of the cup linked to a vacuum pump, and the cup entry port is then sealed. The sealed suction cup is kept in place for for an appropriate length of time.

In still another embodiment, suitable suction cup devices are provided.

DETAILED DESCRIPTION OF THE INVENTION

The essence of the invention is the production of bone regeneration (osteoblastic cell-induced osteogenesis) in a desired area of a bone by the application to this area of a vacuum (within the context of this specification synonymous with subatmospheric pressure) for an effective length of time.

The method can be applied to any bone in humans or animals. It can be applied to a wide variety of medical conditions, e.g., lower jaws that have extensive resorption and that cannot accept implants; a bone that requires lengthening; a bone that needs reshaping, as after an accident; and, a bone after surgical removal of cancerous bone.

At the heart of the invention is a device that produces the vacuum on the surface of the bone. A highly preferred device is an evacuatable suction cup that can be applied snugly to a local area of bone and that can be maintained under vacuum. The cup should be composed of a flexible, sterilizable (e.g., autoclavable) material (e.g., latex, obtainable from ETI, Fields Landing, Calif.), but other materials with similar properties may be used. The thickness of the walls of the suction cup should be sufficient not to collapse under vacuum. Snugness of the cup is accomplished in part by fabricating the cup so that the curvature of the portion resting against the bone is designed to fit the particular bone, and in part by the flexibility of the cup. Cups with a wide variety of sizes and shapes may be fabricated by well-known methods and kept on hand under sterile conditions.

Figure 7:
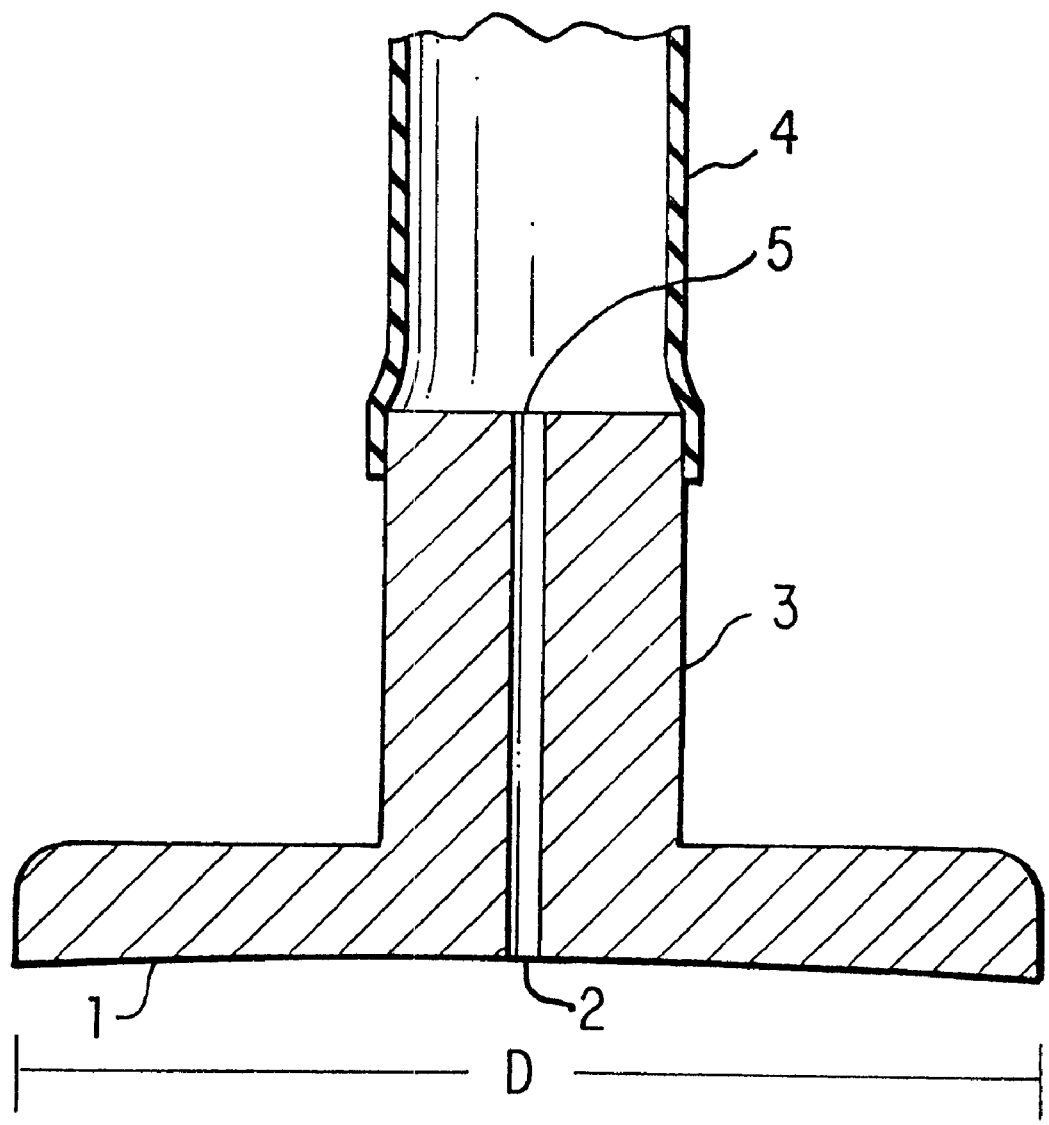
FIG. 7 is a drawing of the inventive vacuum device.

Details of the aforementioned device for applying a vacuum to a local area of a bone so as to stimulate new bone growth in said local area follow. The device comprises a one-piece suction cup 1 with a vertically-oriented stem 3. The device is composed of a sterilizable, flexible or elastic, moldable material. The suction cup 1 is circular and has a curved bottom 1. The cup bottom is of a diameter D appropriate to the bone area being subjected to the vacuum, and the curvature is of a degree appropriate to the curvature of said local area of said bone. The cup 1 is glued to the surface of the bone being treated so as to maintain a vacuum seal. The suction cup 1 and stem 3 are completely solid save for a narrow, circular opening 2 extending from the bottom of the suction cup 1 through to the top of the stem 3. The narrow circular opening 2 is of a diameter of about 10–15% of the diameter D of suction cup 1. The opening 5 at the upper end of stem 3 is by flexible vacuum tubing 4 to a vacuum pump, and is sealed at 5 following attainment of the desired degree of vacuum. The device is depicted in FIG. 7. other vacuum pump is suitable). Following attainment of the desired degree of vacuum, the connection between the cup and the pump is sealed, preferably by stitching and sealing with surgical glue. The degree of vacuum is not critical. For example, Example 1 below demonstrates that a vacuum of as little as 30 in. Hg was sufficient to induce bone generation in a skeletal bone.

The suction cup is maintained in place for an appropriate length of time before being removed. Determination of this appropriate length of time is based on the condition being treated, and this determination does not require undue experimentation by the medical or dental surgeon applying the technique.

The progress of bone regeneration may be followed radiographically, as the suction cup is radiolucent and new bone is not. The osteoid precursor stage of bone regeneration may not, however, always be visible by X-ray.

The following example merely provides an embodiment of the inventive method, and should not be construed as limiting the claims in any way.

EXAMPLE 1

The Protocol

Under sterile conditions, the back of an anesthesized rabbit was shaved, and the right scapula bone reached surgically. Skin, fat, muscles and periosteum were blunt resected from the scapula.

A suction cup device was prefabricated as a unit from latex, the mouth of the cup being of a dimension and degree of curvature so as to fit the local area of the bone. The autoclaved cup device was placed over the desired local area of the bone, and sealed to the bone with surgical glue (Nexaband liquid, Veterinary Products Laboratories, Inc.).

The opening in the base of the cup was attached to a hand-operated Nalgene vacuum pump, and the cup evacuated to about 30 in. Hg. At this point the cup opening was stitched and glued so as to maintain the vacuum. The subcutaneous tissues were closed with a 4-O Dexonsuture, and the skin closed with a 4-O DEXON subcuticular suture. The animal was allowed to recover from the anesthesia in a warm room, then returned to its regular quarters.

After about four weeks, the cup device (still well-sealed) was removed from the scapula, and a thickening of the bone at the site of the treatment noted. Based upon the pathology report, this thickened material was osseoid in nature.

The scapula was removed from the animal, stored in formalin, and brought to the Pathology Department of the The Red Cross Regional General Hospital of Athens for histological analysis of the thickened reagion of the bone. The Pathology Report is reproduced below:

MACROSCOPICAL EXAMINATION: Scapular bone with sites of erosion of the periosteum, having a mean diameter of 1.5 cm.

HISTOLOGICAL EXAMINATION: In the above described area, detachment of the peristeum from the bone is identified, and development from its upper surface of many neoplastic bone trabiculi surrounded by multiple osteoblasts.

Also, a focal production of osteold is noted. Amang the bone trabeculi there is a loose vascular connective tissue, whereas in the mainly peripheral sites the presence of giant cellular phagogranulomata is recognized.

Figure 1:
FIGS. 1–6 are histological microphotographs of sections through a bone after treatment of the bone by the method of the invention. Details of these photographs are provided in Example 1.
Figure 2:
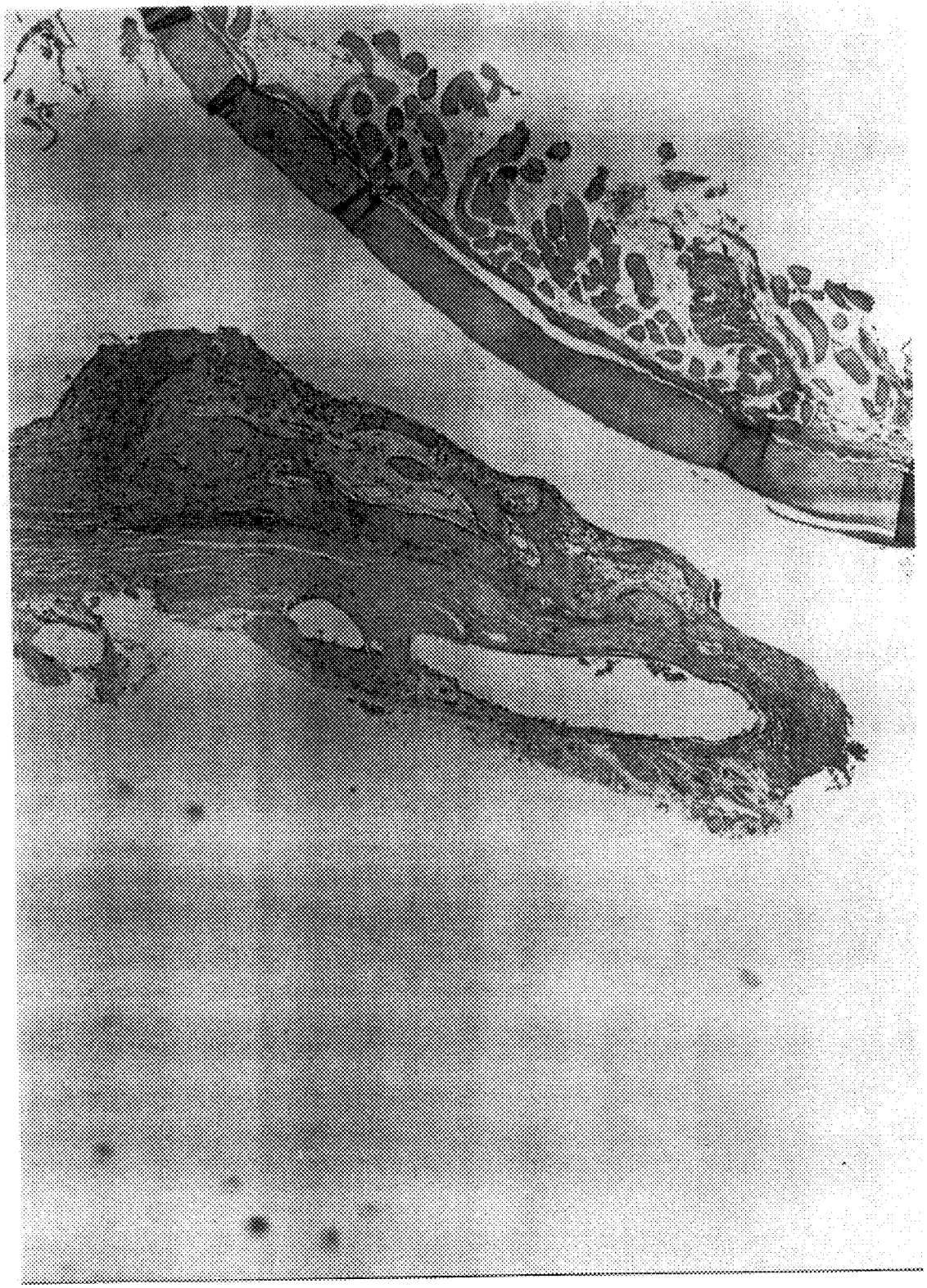
Figure 3:
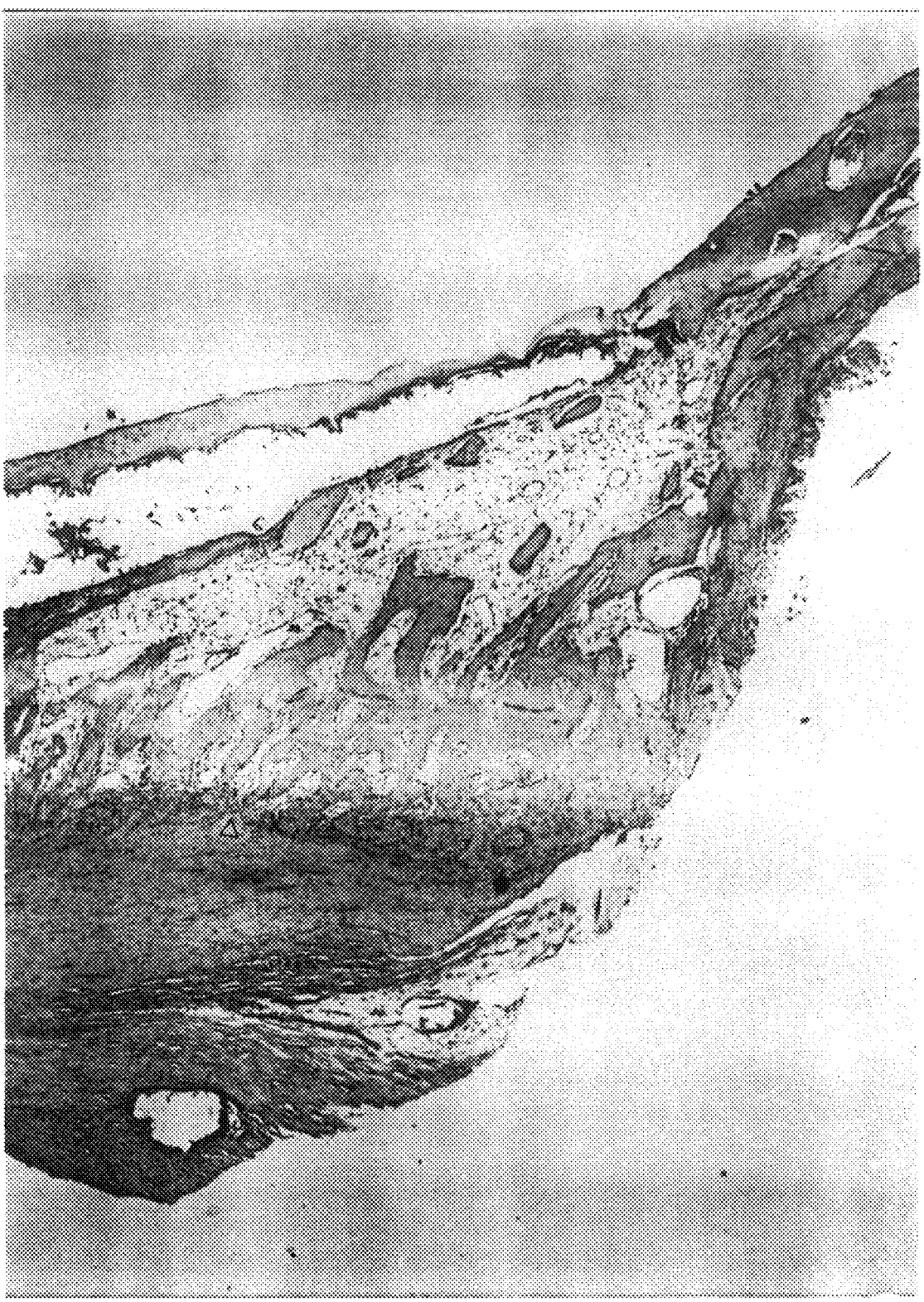
Figure 4:
Figure 5:
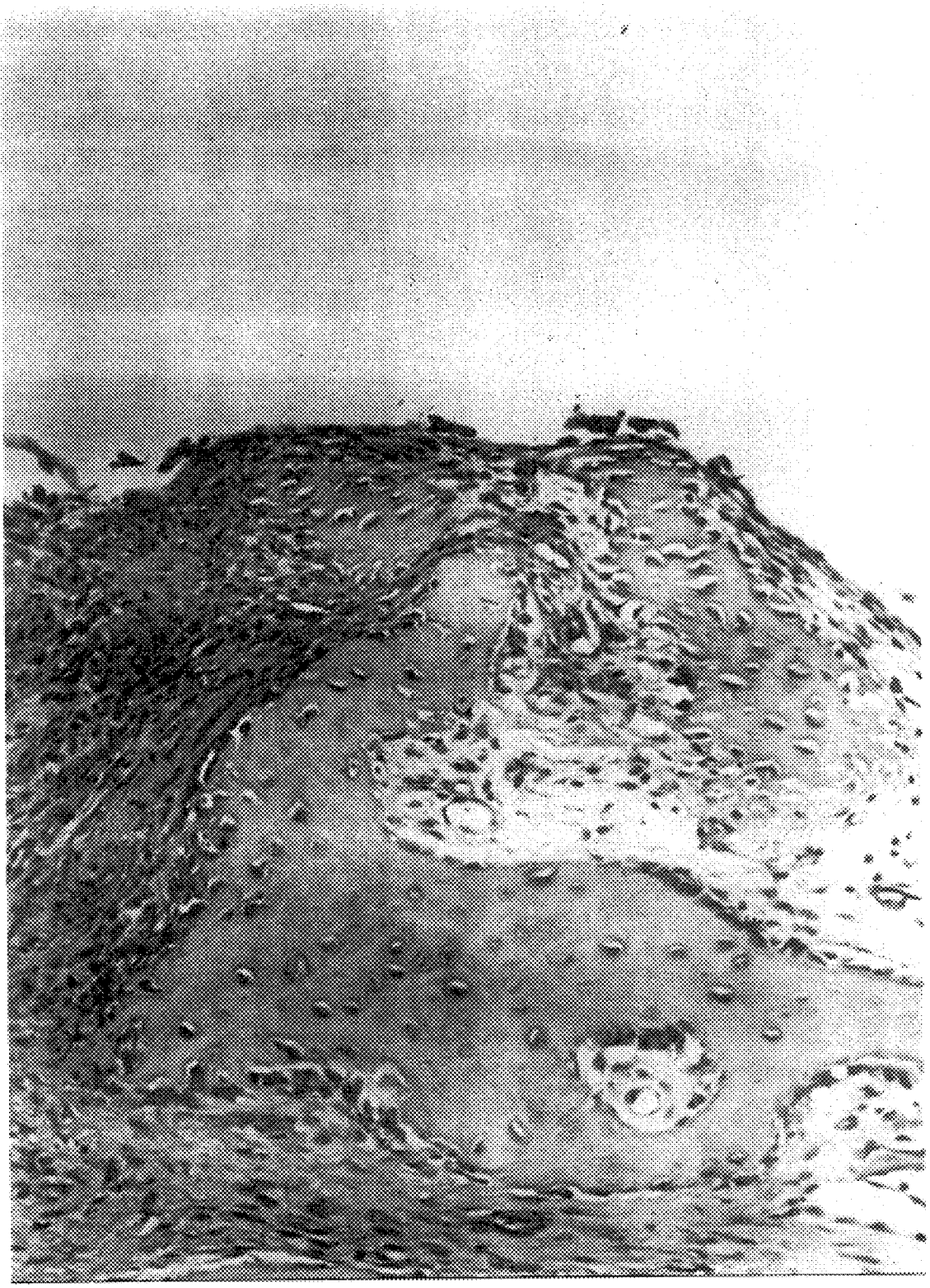
Figure 6:
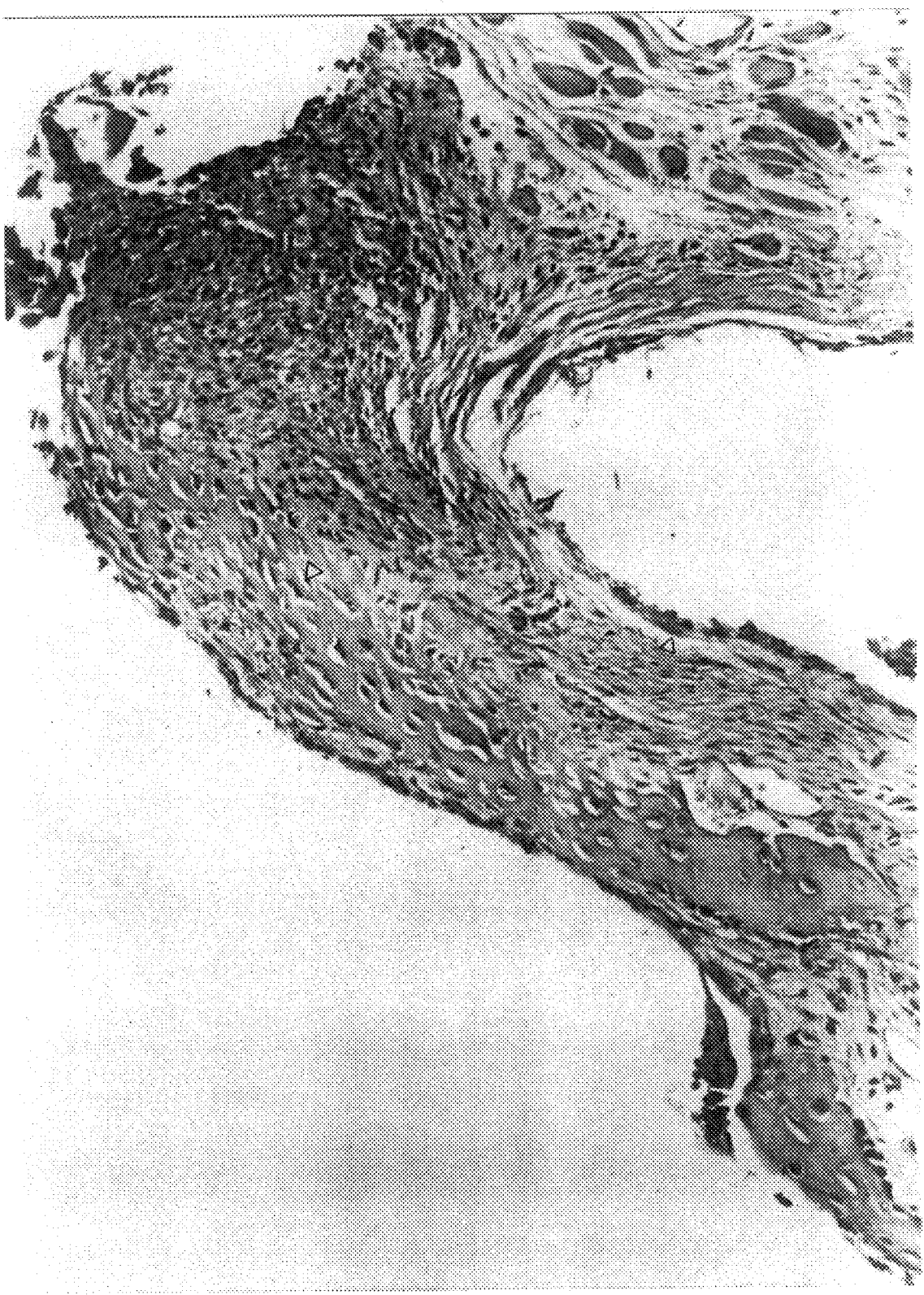

FIGS. 1–5 are histological photographs of the examined bone. FIGS. 1 and 2 are areas of extraction of the periosteum from the subject mature scapular bone. FIG. 3 shows an area of the fattening of the periosteum with the growth, on its internal side, of several neoplastic osteo-beams. FIG. 4 shows neoplastic ossified tissue with the presence of gigantic cellular phago-granuloma possibly developed around a foreign substance. FIG. 5 shows neoplastic osteobeams with intense osteoblastic activity. FIG. 6 shows intense osteoplastic activity with the production of an osteoid and young ossified tissue and in the presence of a sizable gigantic cellular phago-granuloma around the foreign substance.

It is clear from this histological examination, that the method of the invention induced bone regeneration as detected by intense osteoblastic activity (these cells are bone formers) and osteoid formation (precursor of new bone).

I claim:

1. A method of stimulating new bone formation in a local area of a bone in a subject requiring same, comprising the step of applying to said local area of said bone an effective amount of vacuum for an effective period of time.

2. A device for applying a vacuum to a local area of a bone so as to stimulate new bone growth in said local area, said device comprising a one-piece suction cup with a vertically-oriented stem, said device being composed of a sterilizable, flexible or elastic, moldable material, said suction cup being circular and having a curved bottom, said cup bottom being of a diameter appropriate to the bone area being subjected to said vacuum and said curvature being of a degree appropriate to the curvature of said local area of said bone, said cup being adapted to be glued to the surface of the bone being treated so as to maintain a vacuum seal, said suction cup and stem being completely solid save for a narrow, circular opening extending from the bottom of said suction cup through to the top of said stem, said narrow circular opening being of a diameter of about 10–15% of the diameter of said suction cup, and said opening at the upper end of said stem being capable of being connected by flexible vacuum tubing to a vacuum pump and being sealed following attainment of the desired degree of vacuum.

\* \* \* \* \*